(12) United States Patent
Croan (10) Patent No.: US 11,062,795 B2
(45) Date of Patent: Jul. 13, 2021

(54) HEALTHCARE DATA SYSTEM

(75) Inventor: Clifton D. Croan, Denver, CO (US)

(73) Assignee: Enigami Systems, Inc., Denver, CO (US)

( * ) Notice: Subject to any disclaimer, the term of this patent is extended or adjusted under 35 U.S.C. 154(b) by 547 days.

(21) Appl. No.: 12/038,650

(22) Filed: Feb. 27, 2008

(65) Prior Publication Data
US 2008/0215365 A1    Sep. 4, 2008

Related U.S. Application Data

(60) Provisional application No. 60/892,793, filed on Mar. 2, 2007.

(51) Int. Cl.
| | |
|---|---|
| *G16H 15/00* | (2018.01) |
| *G16H 40/60* | (2018.01) |
| *G16H 10/60* | (2018.01) |
| *G06Q 10/10* | (2012.01) |

(52) U.S. Cl.
CPC ............ *G16H 10/60* (2018.01); *G06Q 10/10* (2013.01); *G16H 15/00* (2018.01); *G16H 40/60* (2018.01)

(58) Field of Classification Search
CPC ........ G06Q 50/22; G06Q 50/24; G06Q 10/10; G06F 19/3481; G06F 19/3487; G06F 19/3418; G16H 15/00; G16H 40/60; G16H 50/20; G16H 10/60
USPC .......................................... 705/2–3; 600/300
See application file for complete search history.

(56) References Cited

U.S. PATENT DOCUMENTS

| | | | |
|---|---|---|---|
| 6,770,029 B2 | 8/2004 | Iliff | |
| 7,079,524 B2 | 7/2006 | Bantukul et al. | |
| 7,092,370 B2 | 8/2006 | Jiang et al. | |
| 7,103,372 B1 | 9/2006 | Kupsh | |
| 7,209,950 B2 | 4/2007 | Bennett et al. | |
| 7,379,885 B1 * | 5/2008 | Zakim .............................. | 705/2 |
| 2002/0029157 A1 | 3/2002 | Marchosky | |
| 2002/0138304 A1 * | 9/2002 | Fontanesi ......................... | 705/2 |
| 2004/0249250 A1 | 12/2004 | McGee et al. | |

(Continued)

FOREIGN PATENT DOCUMENTS

WO    WO-0070508 A1 * 11/2000 ............. G16H 40/63

OTHER PUBLICATIONS

Trigg et al., Development of a wireless web based infrastructure to support collection of patient self-reported QoL & symptom information in a clinical setting, 2002, AMIA 2002 Annual Symposium Proceedings, p. 1180. (Year: 2002).*

(Continued)

*Primary Examiner* — Christopher L Gilligan
(74) *Attorney, Agent, or Firm* — Vobach IP Law, LLC (57) ABSTRACT

In accordance with one embodiment, a system and method is used for collecting, measuring, and reporting on data associated with healthcare treatment. A healthcare data system collects data from a patient using an interactive voice response system (IVR). The IVR periodically contacts the patient with questions as to severity of symptoms. The severity data is processed along with prior collected data to report treatment progress to the patient, to a provider, to a provider organization and to a payer. Symptom weights are entered by a provider and used in measuring progress. Other methods to collecting severity data may be used, such as email and text messaging.

5 Claims, 10 Drawing Sheets

(56) References Cited

U.S. PATENT DOCUMENTS

| | | | |
|---|---|---|---|
| 2005/0075904 A1* | 4/2005 | Wager | G06Q 10/10 705/2 |
| 2006/0036619 A1 | 2/2006 | Fuerst et al. | |
| 2006/0080059 A1 | 4/2006 | Stupp et al. | |
| 2006/0106645 A1 | 5/2006 | Bergelson et al. | |
| 2006/0161456 A1* | 7/2006 | Baker | G06F 19/00 705/2 |
| 2006/0178569 A1* | 8/2006 | Dean | 600/300 |
| 2006/0229505 A1 | 10/2006 | Mundt et al. | |
| 2006/0241974 A1* | 10/2006 | Chao et al. | 705/2 |
| 2007/0016443 A1* | 1/2007 | Wachman | G06F 19/3456 705/2 |
| 2007/0021979 A1* | 1/2007 | Cosentino | A61B 5/0031 705/2 |
| 2007/0033066 A1* | 2/2007 | Ammer et al. | 705/2 |
| 2007/0179349 A1* | 8/2007 | Hoyme | G16H 40/63 600/300 |
| 2007/0226012 A1* | 9/2007 | Salgado et al. | 705/3 |
| 2007/0255322 A1* | 11/2007 | Gerber et al. | 607/2 |
| 2007/0280431 A1* | 12/2007 | Alpsten et al. | 379/38 |
| 2008/0052318 A1* | 2/2008 | Iliff | 707/104.1 |
| 2008/0177149 A1* | 7/2008 | Weinert et al. | 600/300 |
| 2009/0055220 A1* | 2/2009 | Rapaport et al. | 705/2 |
| 2009/0112624 A1* | 4/2009 | Brown | 705/2 |

OTHER PUBLICATIONS

Intille, Stephen S. et al, "A Context-Aware Experience Sampling Tool," CHI 2003, Apr. 5-10, 2003, Ft. Lauderdale, FL, USA, 2 pages, retrieved Nov. 20, 2014.

Mooney, K.H. et al, "Telephone-linked Care for Cancer Symptom Monitoring: A Pilot Study," vol. 10, Issue 3, First published online, Apr. 30, 2002; retrieved Nov. 20, 2014, 8 pages.

Finn, Steven E. et al, "Therapeutic Assessment with the MMPI-2 in Managed Health Care," in J.N. Butcher (Ed.) Objective psychological assessment in managed health care: A practitioner's guide (pp. 131-152), Oxford University Press, retrieved Dec. 19, 2014, 22 pages.

* cited by examiner

HEALTHCARE DATA SYSTEM

CROSS-REFERENCES TO RELATED APPLICATIONS

This application claims the benefit under 35 U.S.C. § 119(e) of U.S. Provisional Patent Application No. 60/892,793, filed Mar. 2, 2007, entitled "HEALTHCARE DATA SYSTEM," the disclosure of which is hereby incorporated by reference in its entirety for all purposes.

BACKGROUND OF THE INVENTION

Effective healthcare treatment is a significant issue for consumers, providers (e.g., physicians, healthcare professionals, and hospitals) and healthcare payers (e.g., insurers, government agencies and other payers). One significant problem is establishing accountability in provider treatment, i.e., making sure that treatment is effective when measured against established standards or expected results.

This is particularly true when the treatment is for mental disease or disorders. For such disorders, effectiveness will often depend on how the patient is feeling or how the provider perceives the patient is feeling after treatment. Progress is often in small increments and occasional patient feedback may not reliably reveal small, incremental improvement over weeks, months or other long intervals.

Accountability becomes an even greater issue when one considers the cost of treatment, such as the cost of government programs providing medical and mental healthcare. By some estimates, government funded healthcare spending accounts for over 60% of today's total healthcare costs in the United States. Many government programs (e.g., Medicaid) are reported to have large losses resulting from fraud, waste and abuse, and such losses often become a financial hardship to the agencies administering the program.

There has thus arisen the need for systems and methods for collecting data on healthcare symptoms and treatment, measuring progress of treatment, and reporting progress (or the lack of progress) in order to evaluate the effectiveness of treatment.

BRIEF SUMMARY OF THE INVENTION

There is provided, in accordance with embodiments of the invention, a network, system and method for evaluating healthcare treatment of a patient.

In one embodiment, a method comprises establishing a diagnosis for a patient, establishing symptoms corresponding to the diagnosis, periodically collecting data from the patient relating to symptoms (e.g., through an interactive voice response or other data entry system), processing the collected data to measure progress of treatment, and reporting the measured progress (e.g., to a provider, to the patient, to a provider organization, or to a payer).

In some embodiments, the method may include establishing a weight for each symptom, and taking into account the weight when measuring the progress of treatment.

DETAILED DESCRIPTION OF THE INVENTION

Figure 1:
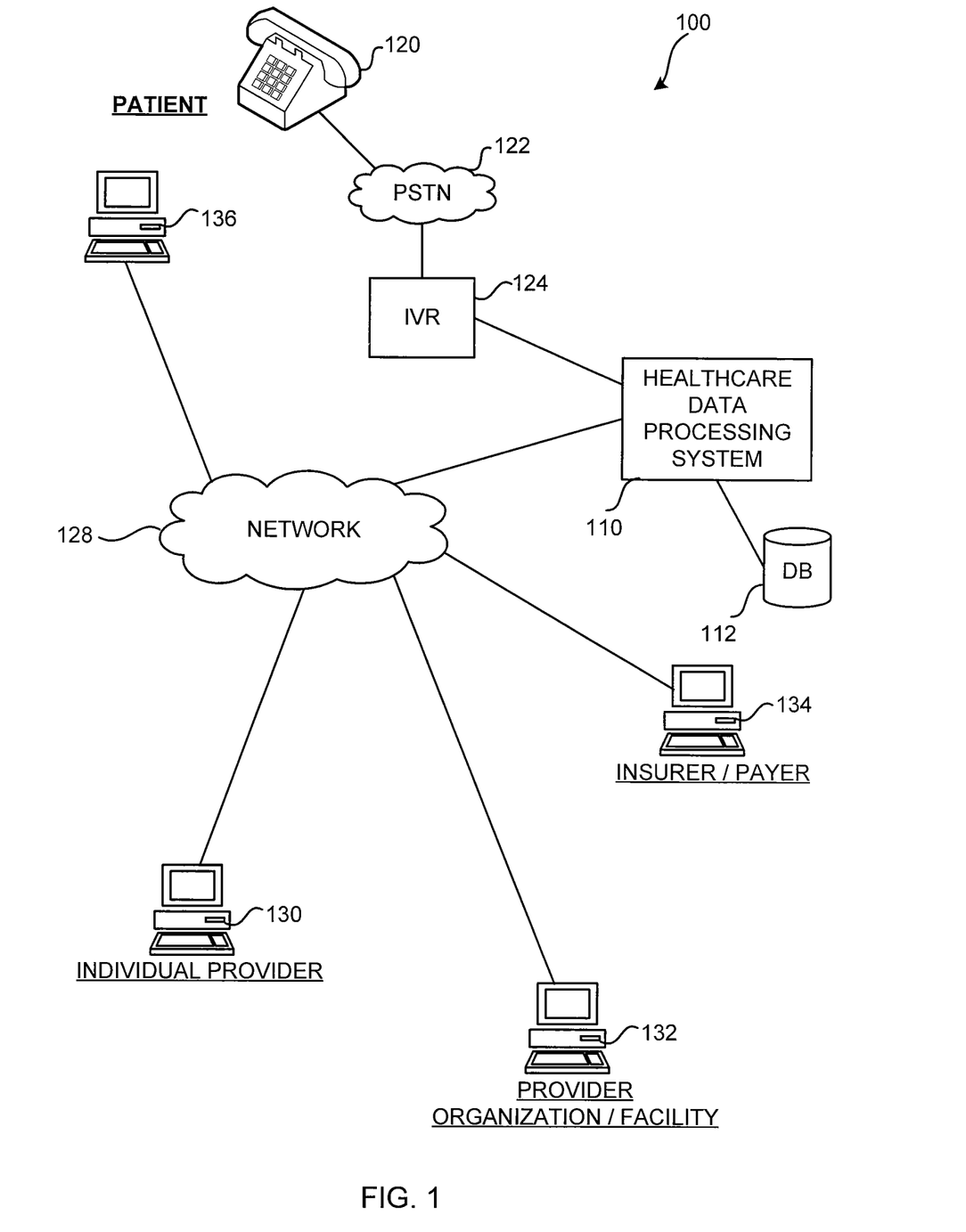
FIG. 1 is a block diagram of a healthcare data network in accordance with one embodiment of the invention.

FIG. 1 shows a health data network 100 according to one embodiment of the invention. The network 100 includes a healthcare data processing system 110 that collects, processes, measures and reports data received from a patient in the form of responses/entries made at a patient telephone 120. Data collected from a patient or relevant to patient treatment may be stored in a database 112 associated with system 110. The system 110 is connected for receiving data entered (e.g., on a DTMF keypad) at telephone 120 through the public switched telephone network (PSTN) 124 via an interactive voice response system (IVR) 124. In one embodiment, the IVR system auto dials patients at pre-established intervals (e.g., weekly) and requests feedback on symptoms by asking a question for each symptom and requesting that the patient provide input (e.g., on a scale of 1-9) on the severity of the symptom experienced by the patient at that time.

Of course, other arrangements for collecting feedback are possible in the network 100, such as a manually dialed call from the provider or another person, with that person entering responses from the patient for use by the system 110. In some embodiments, the manner of collecting feedback may change if the feedback does not meet a predetermined standard (e.g., from failure to respond to automated phone calls, from returned data being ambiguous or unhelpful, etc.).

Also seen in FIG. 1 is a network 128 that connects computer systems 130, 132, 134, and 136 with healthcare data processing system 110. In one embodiment, the network 128 is the Internet, and the systems 130, 132, 134, and 136 are PCs or other stationary or mobile devices for entering or receiving/displaying data. As illustrated, the computer 130 is used by individual healthcare providers (e.g., a therapist, doctor, or other provider of mental or medical healthcare), the computer 132 is used by a provider organization/facility, the computer 134 is used by an insurer/payer, and the computer 136 is used by a patient.

The provider may use the system 130 to enter data pertaining to the patient (e.g., a diagnosis). As an example, the diagnosis could be entered after a patient has first visited the provider. The provider may also enter, as will be described in greater detail later, various weights for the symptoms being experienced by the patient. The provider may also use system 130 to view reports generated in response to subsequent feedback data from the patient (inputted at telephone 120) on the severity of patient symptoms over time. In some embodiments, the provider may use system 130 during the first visit to enter the patient's most noticeable symptoms, and the system 110 may return possible diagnoses, treatment plans, and other symptoms/conditions to be considered for evaluation or monitoring.

The provider organization may use the system 132 to monitor care or treatment being given by a provider employed by or affiliated with the organization. As one example, after a patient provides feedback over time as to the severity of symptoms, the provider organization (e.g., a supervisor or other person within the organization that manages the care given by individual providers) may view reports of symptoms to determine whether the treatment is resulting in improvement in those symptoms.

The insurer/payer may be an entity that pays for some or all of the treatment (insurance company, government agency managing Medicaid, and so forth). The payer may use the system 134 to view patient feedback on symptoms to determine whether the treatment is resulting in improvement in those symptoms. The payer can thereby determine if the treatment cost is resulting in progress for the patient. Thus, the network 100 permits accurate and efficient utilization review to take place. The insurer/payer may also view reports for individual providers within an organization, as well as collective data for multiple providers within each of one or more organizations. As an example, a payer may contract for healthcare service from multiple provider organizations, and may use the reports to compare the overall efficacy of treatment from each of the organizations (as well as the overall efficacy of treatment across all organizations for specific conditions or disorders).

The patient may use system 136 to view reports on the progress of his/her treatment (e.g., through password protected access to a website associated with system 110). For example, in the case of a mental or emotional disorder, a patient may have some difficulty in seeing improvement over time because the improvement may be only in small increments. The patient can view reports similar to those seen by the provider, provider organization and payer, illustrating how the severity of the symptoms in his/her own case have been reported over a long period of time (e.g., months or even years). Of course, the patient may also view the reports while communicating with the provider (e.g., over the telephone 120) to better understand various aspects of the reports being viewed. In some cases, where a patient does not have a computer system 136, he or she may receive results in audible form at telephone 120, e.g., reports automatically generated at IVR 124.

Thus, the patient can be more actively and directly involved in assessing his/her own progress, and better understand the condition or disorder, and see the results of treatments based on data collected for that specific patient.

In some embodiments, a patient may enter feedback on symptom severity at the system 136 in lieu of or in addition to entering feedback data at telephone 120.

Figure 2:
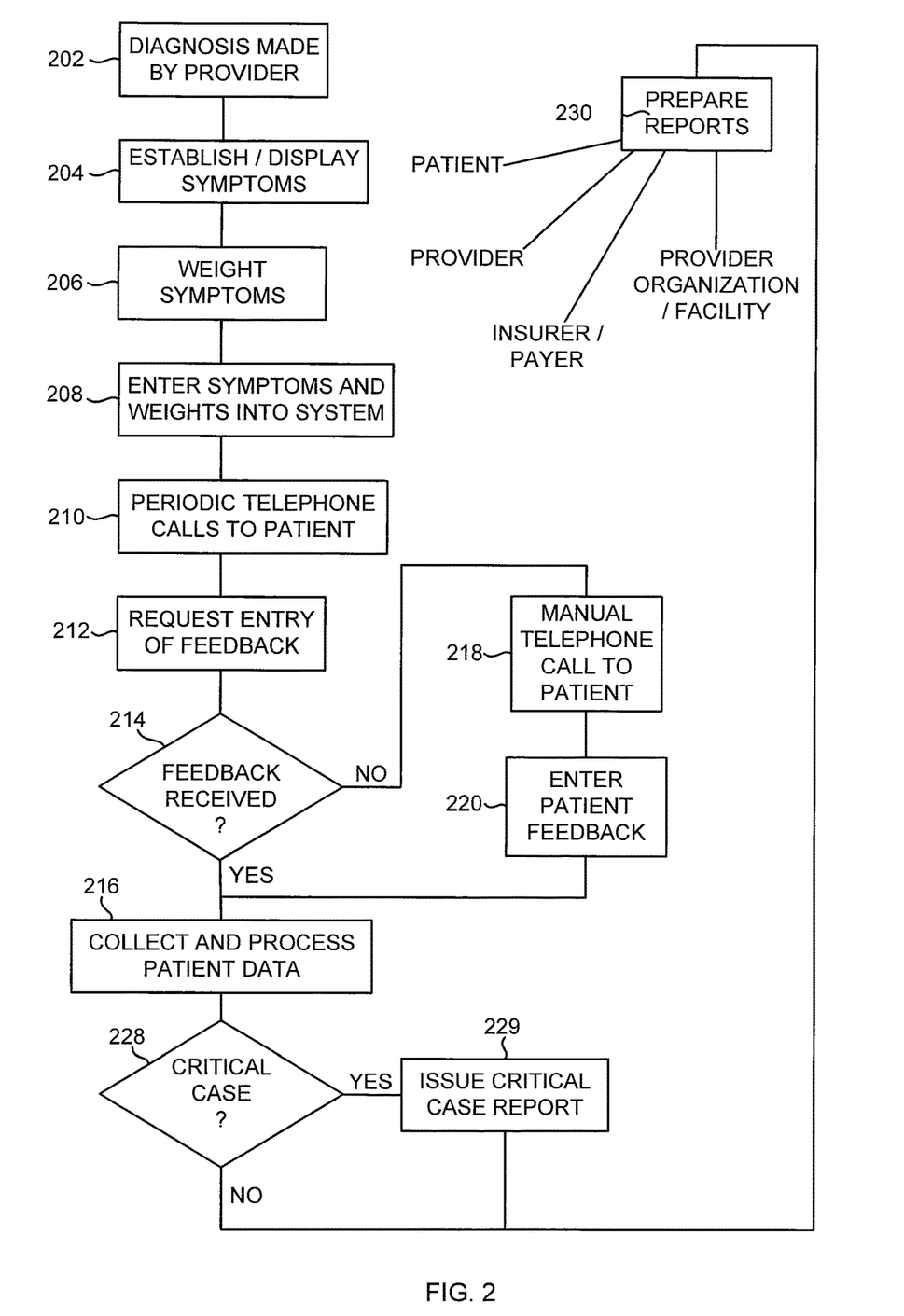
FIG. 2 is a flow diagram illustrating the operation of the network of FIG. 1.

FIG. 2 illustrates the operation of the network 100, including the system 110. The operation will be described using an example of a patient who has sought treatment for a mental healthcare condition, such as mild depression. The patient may visit a provider (e.g., therapist, psychologist, psychiatrist, or other mental healthcare provider), and a diagnosis is made at step 202. The provider then determines the measurable symptoms of the patient. In many cases this will have been done in advance by the system 110 in response to the diagnosis being entered, using pre-established standard symptoms for the diagnosis. For example, in the case of mild depression, a diagnosis of dysthymia is made by the provider at step 202, and the system 130 used by the provider communicates with system 110 in order to retrieve and list the standard symptoms that are experienced by patients diagnosed with dysthymia. Carrying this example further, the following Exhibit A provides a description of dysthymia and its typical symptoms, taken from Diagnostic and Statistical Manual of Mental Disorders (DSM-IV-TR®).

---
Exhibit A
Dysthymic Disorder
(DSM 300.4)
---

Depressed mood for most of the day, for more days than not, as indicated either by subjective account or observation by others, for at least 2 years. Note: In children and adolescents, mood can be irritable and duration must be at least 1 year.
Symptoms
Presence, while depressed, of two (or more) of the following:

(1) poor appetite or overeating
(2) insomnia or hypersomnia
(3) low energy or fatigue
(4) low self-esteem
(5) poor concentration or difficulty making decisions
(6) feelings of hopelessness Symptoms based on the foregoing may be displayed to the provider at system 130 (step 204) and the provider then establishes a weight to be given to each symptom, based on the session with the patient (step 206). The weighting will typically be made using the severity or significance of the symptom as experienced by the patient. The following TABLE I is an example of the symptoms that have been established under current psychiatric practice for dysthymia, and illustrate weights given (as percentages) to each symptom after discussion between the patient and the provider:

TABLE I

| Symptom | Weight |
| --- | --- |
| Decreased Appetite | 10% |
| Sleeping Problems | 50% |
| Feelings of Hopelessness | 20% |
| Difficulty Concentrating | 5% |
| Low Self Esteem | 5% |
| Low Energy Level | 5% |
| Fatigue | 5% |
| Total | 100% |

The system 110 may be programmed to aid the provider in entering the weights for the symptoms at the system 130, step 208. For example, TABLE I as illustrated above could be displayed in response to an entered diagnosis with pre-established symptoms and pre-established weights. The symptoms and weights could be modified based on discussions between the patient and provider during the initial (or subsequent) therapy sessions. Alternatively, a pie chart could be displayed with the provider and patient viewing the chart and modifying each slice (symptom) to reflect how the patient and provider assess the severity of the symptom in relation to other symptoms. In some embodiments, the system 110 could permit other symptoms (and weights) not normally associated with the diagnosis to be entered (at step 208) and subsequently considered in soliciting feedback.

Later, the system 110 may periodically initiate telephone calls to the patients through the IVR 124, step 210. An example of questions asked of the patient is illustrated in the "Dysthymia Telephone Script" seen in the following Exhibit B.

---
Exhibit B
Telephone Script for Dysthymia

---

"Welcome to the Enigami symptom rating system!"
(English and Spanish) "If this is an emergency, please hang up and dial 911."
"If you prefer English, press 1. If you prefer Spanish, press 2."
"Please enter your Colorado Medicaid number."
"While answering, remember, 1 is very poor and 9 is very good."
"If you wish to have a questions repeated, press the pound sign."
"On a scale of 1 to 9 - how was your appetite yesterday?"
"On a scale of 1 to 9 - how was your sleep last night?"
"On a scale of 1 to 9 - how were your feelings of hopelessness yesterday?"
"On a scale of 1 to 9 - how was your concentration or difficulty making decisions yesterday?"
"On a scale of 1 to 9 - how was your self esteem yesterday?"
"On a scale of 1 to 9 - how was your energy level yesterday?"
"On a scale of 1 to 9 - how was your fatigue level yesterday?"
"Finally, did you have an office visit this week? Press 1 for yes, and 9 for no."
"Thank you! Your responses have been recorded and indicate you are feeling less depressed. Congratulations! and goodbye."

---

As indicated, the patient is requested to enter feedback data (e.g., representing the current severity of each earlier established symptom), step 212. If the call is automatically dialed by the IVR 124, the system 110 will periodically check to make sure the call is being accepted and data entered by the patient, step 214. If it is, data is collected and processed (for subsequent reporting of results) at step 216. If not, then the provider or another person will be alerted to call the patient directly to obtain the feedback (step 218), and that data is entered at step 220 (e.g., at system 130).

Calls from the IVR could be made at the time of day when patients are most likely to respond or, alternatively, at specific times chosen by patients in advance. As an optional feature, a patient could be given the opportunity to respond to a call by making a selection for receiving the call at a later time, when more convenient or when the patient is more comfortable providing the feedback. This may not only improve the satisfaction of the patient, but also improve the quality of the feedback.

In the specific example of the "Dysthymia Telephone Script" in Exhibit B, the feedback is requested weekly, and for purposes of collecting data on the number of visits (and progress measured against the frequency or timing of visits), the patient is asked if there was a visit or session with the provider that week. However, it should be appreciated that the frequency of requested feedback could be greater or less (e.g., daily, monthly), depending on the condition being treated. As a further example, the frequency may vary, such as early feedback (after an initial session) being requested daily and later feedback requested less often (e.g., weekly, monthly). As yet another example, the frequency can be changed based on feedback, e.g., the frequency can be increased if feedback indicates that the severity or degree of symptoms is worsening.

Also, as illustrated in the "Dysthymia Telephone Script" in Exhibit B, the system 110 permits some results to be processed and reported to the patient as part of the call. For example, if the severity of symptoms has improved since the last feedback, the patient may be told of the improvement by a message, after the current feedback is entered and compared at system 110 to earlier feedback.

The system 110 determines whether a critical case report is indicated at step 228, and issues one if appropriate (step 229). An example of such a report will be given later, but briefly if the feedback from the patient indicates a significant increase in severity or some other condition that requires the attention of or intervention by the provider, an email alert may automatically be generated by system 110 to the provider (and if desired, to the provider organization and to the payer).

Finally, reports on patient feedback may be generated by system 110 (step 230) for the patient, provider, provider organization, and the payer.

Figure 3:
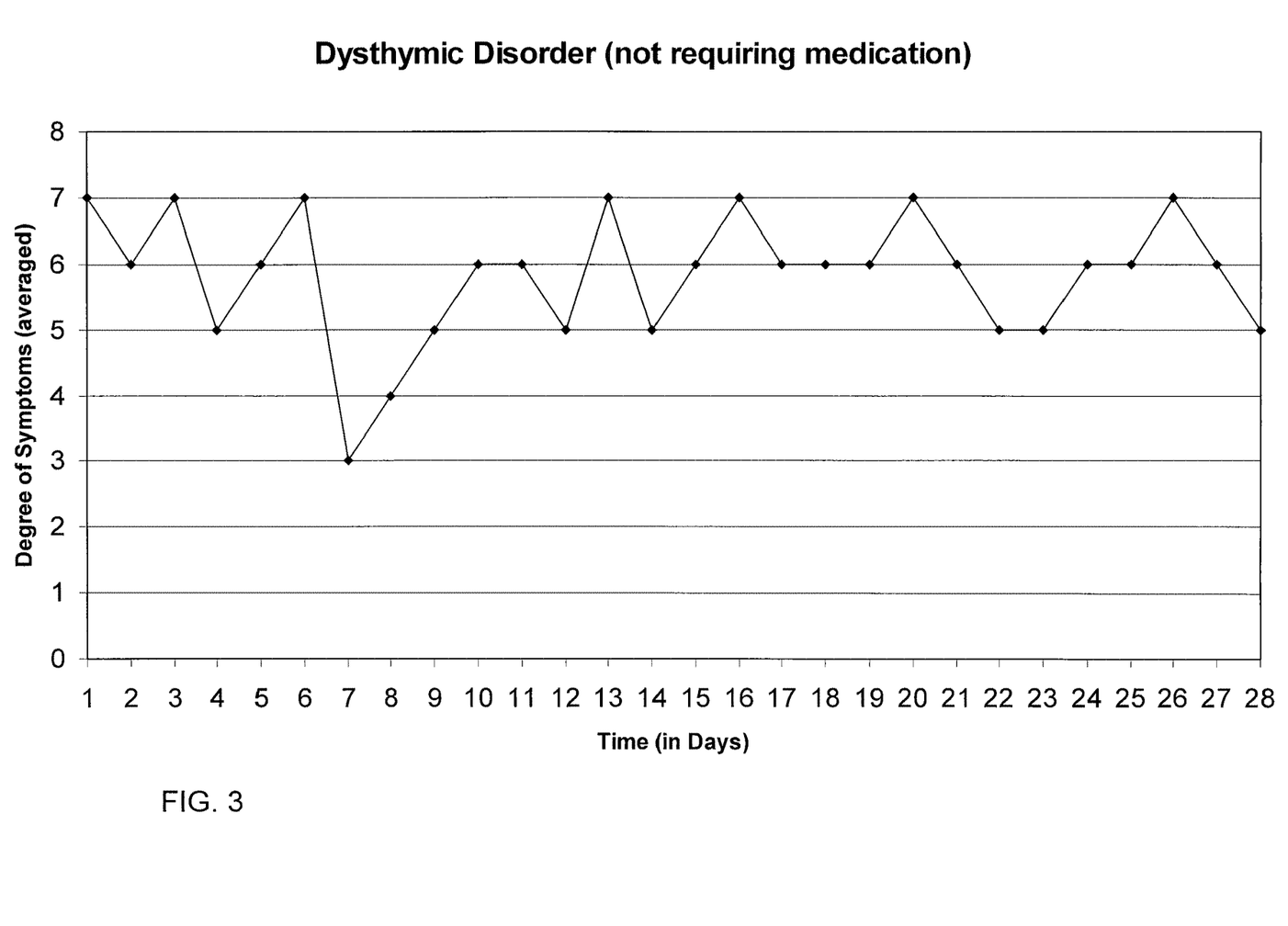
FIG. 3 illustrates an exemplary report displayed on a computer screen and resulting from the collection and processing of data within the healthcare data network seen in FIG. 1, where the feedback is from a patient diagnosed with dysthymia.

Examples of reports that could be generated by the system 110 are illustrated in FIGS. 3, 4, 5, and 6. In FIG. 3, the illustrated report shows the overall or averaged severity of symptoms for a patient having dysthymia over a period of several weeks (data has been collected daily). The results take into account the weights established at step 206, so that the symptoms having the greatest severity or impact on the patient influence the result more than those having the least severity or impact. In FIG. 3, the patient's overall and weighted severity of symptoms has not significantly improved.

Figure 4:
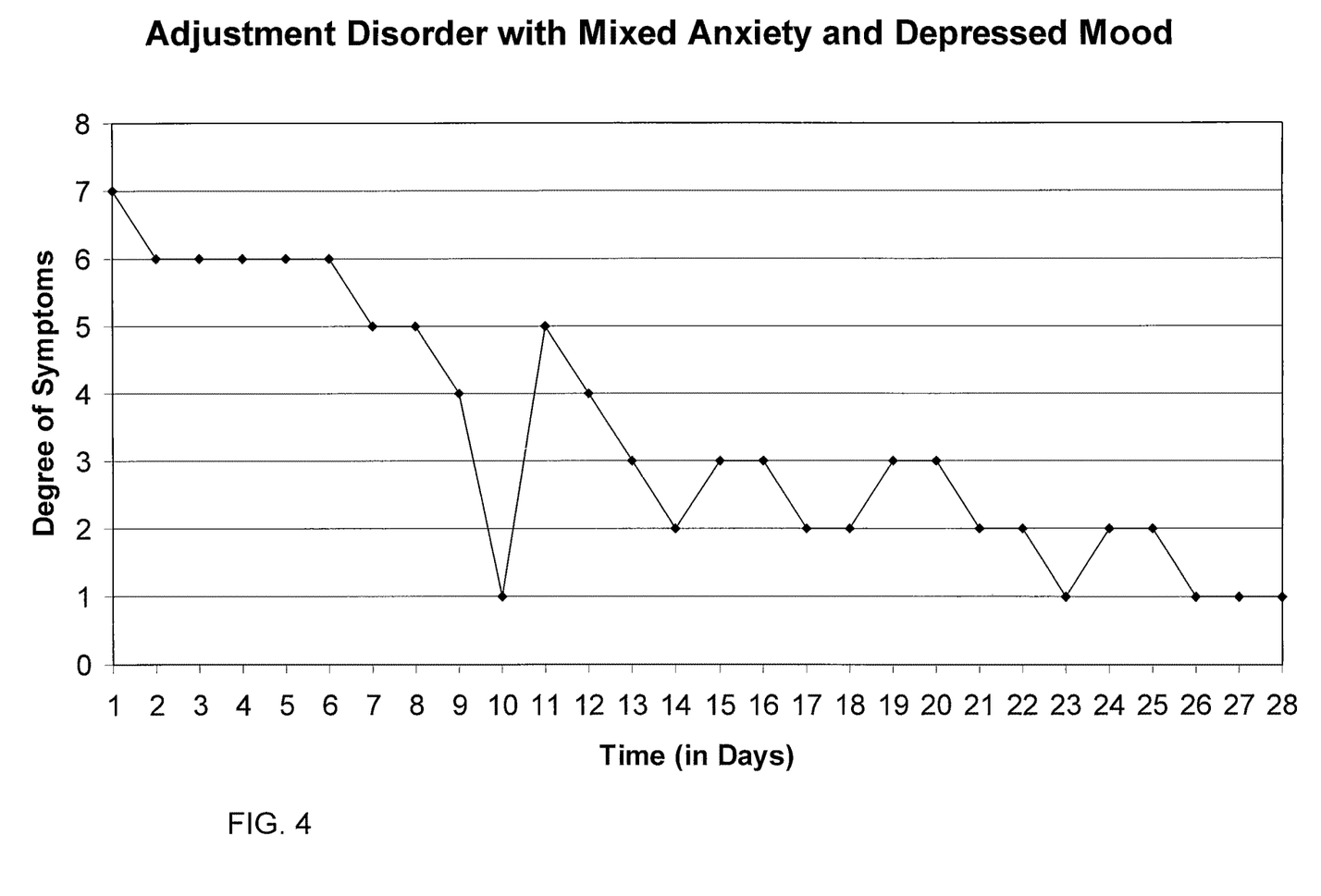
FIG. 4 is a similar report, but for a patient diagnosed with Adjustment Disorder.

In FIG. 4, a report for a patient with Adjustment Disorder is illustrated. In this case, the patient's symptoms have improved over time (lower numbers indicating less severity).

Figure 5:
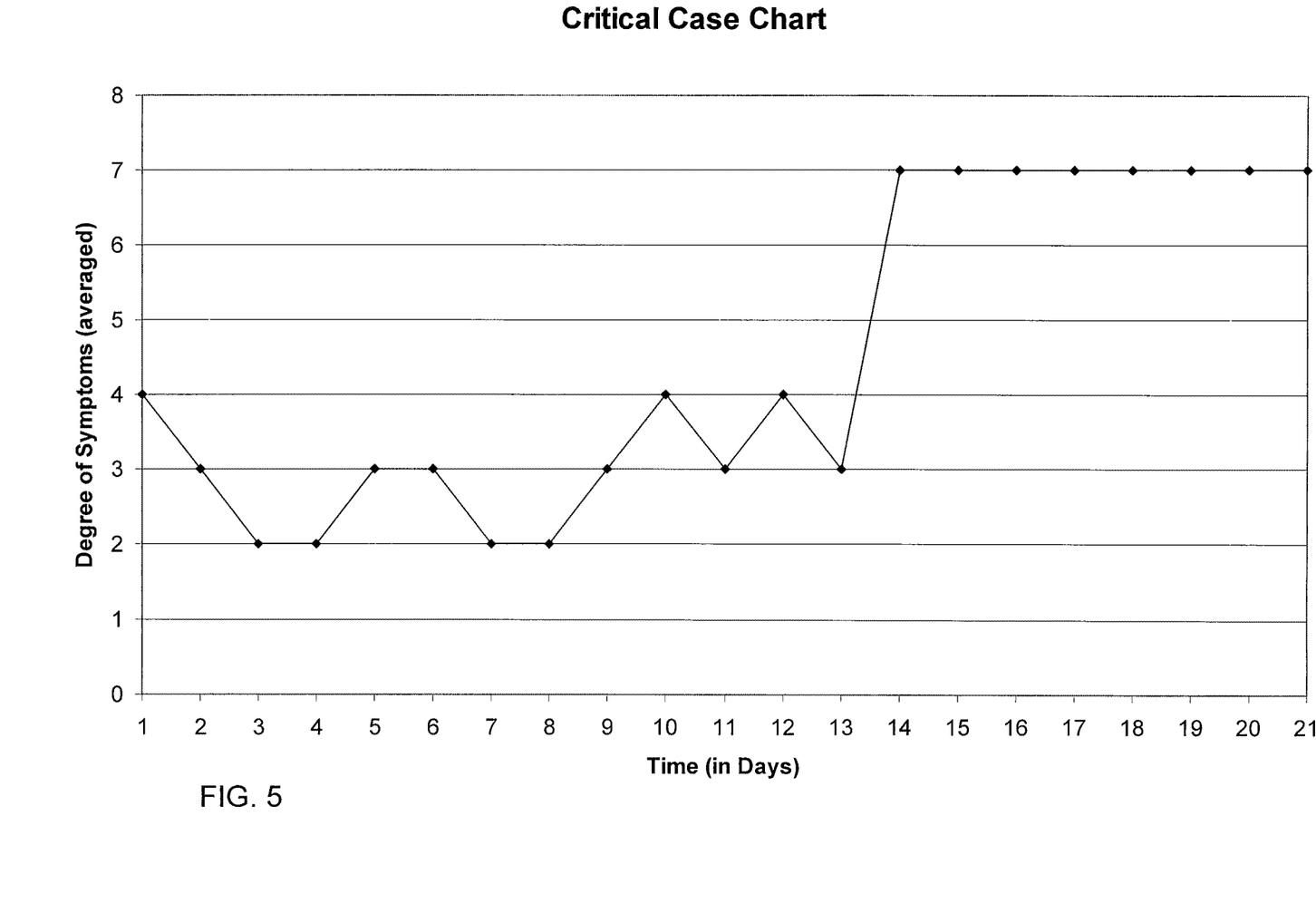
FIG. 5 is a similar report, illustrating a critical case where there has been a spike in severity of symptoms.

In FIG. 5, a spike in severity of symptoms is illustrated, indicating a critical case, and a need for the provider to intervene or communicate directly with the patient. As described earlier, such a report could trigger an email or other alert to the provider (and others). Other predetermined standards or conditions could be established for causing alerts to be generated, based on a lack of feedback, the quality of the feedback, the length of time since last appointment, and so forth.

Figure 6:
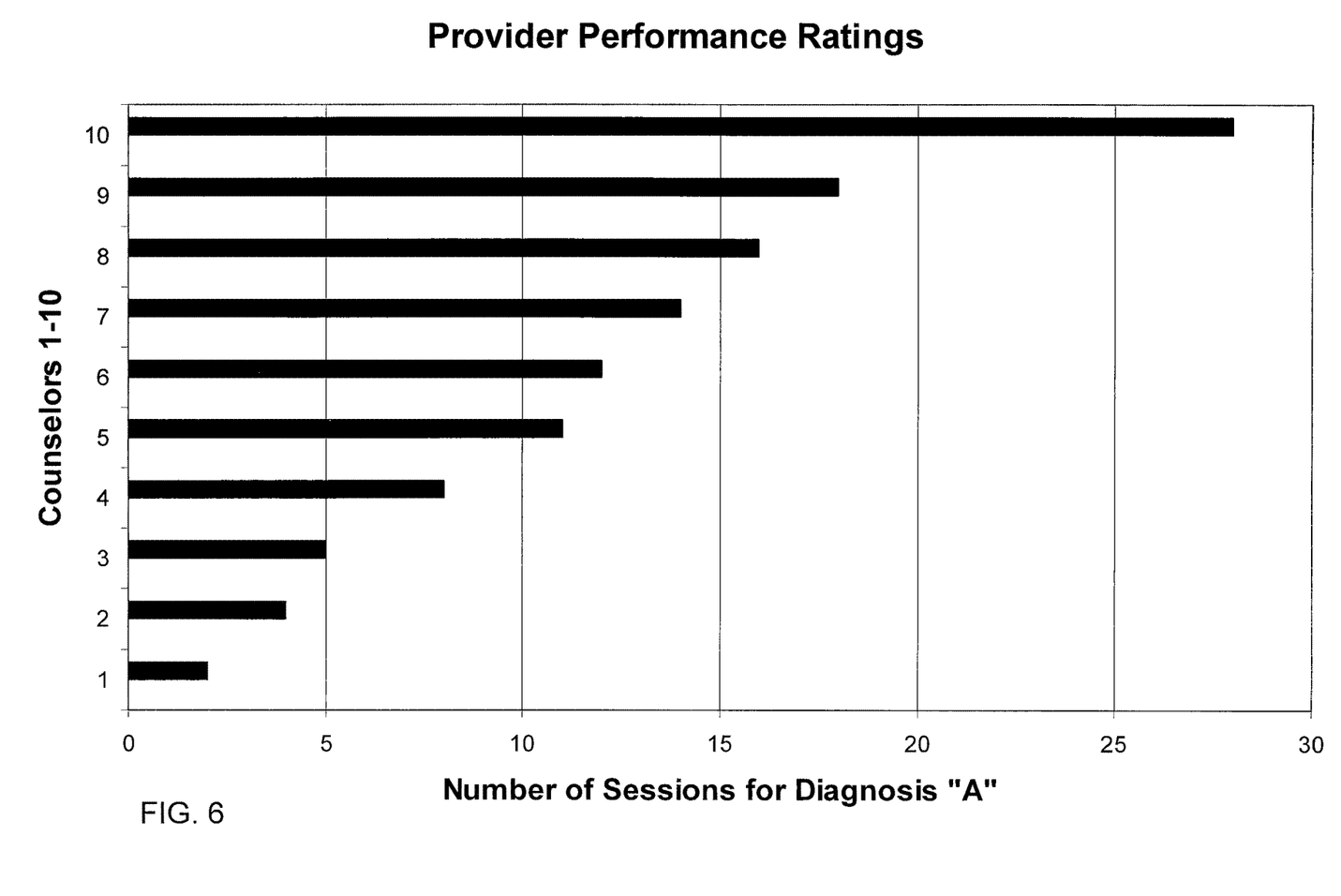
FIG. 6 is a report illustrating provider performance ratings, where the average number of treatment sessions for all patients having a specified diagnosis are given for each of ten different therapists (counselors).

In FIG. 6, provider performance ratings are illustrated. This report might be sent to a provider organization or to a payer showing, for ten different therapists (counselors), the average number of treatment sessions for all patients having a specified diagnosis "A". As seen, counselor 10 averages approximately 28 sessions for patients having the diagnosis, whereas counselor 1 has approximately 2. This may indicate that counselor 10 is not efficient or effective in treating the disorder. Counselor 1, on the other hand, may fail to establish an effective therapeutic relationship with patients, and the report appears to show patients prematurely ceasing the treatment.

As should be understood, the use of the network 100 and system 110 for collecting, processing, measuring and reporting on symptom data is not limited to mental healthcare treatment. As an example, the following Exhibit C provides a description of a medical condition (Pityriasis Rosea) and its typical symptoms, taken from the Merck Manual of Medical Information and the International Classification of Diseases (ICD-9-CM).

Exhibit C
Pityriasis Rosea
(ICD 696.3)

Pityriasis rosea is a mild disease that causes many small patches of scaly, rose-colored, inflamed skin.
The cause of pityriasis rosea is not certain but may be an infectious agent; however, the disorder is not thought to be contagious. It can develop at any age but is most common in young adults. It usually appears during spring and autumn.
Symptoms Pityriasis rosea causes a rose-red or light-tan patch of skin about 1 to 4 inches in diameter that doctors call a herald or mother patch. This round or oval area usually develops on the torso. Sometimes the patch appears without any previous symptoms, but some people have a vague feeling or illness, loss of appetite, fever, and joint pain a few days before. In 5 to 10 days, many similar but smaller patches appear on other part of the body. These secondary patches are most common on the torso, especially along and radiating from the spine. Most people with pityriasis rosea have some itching, and in some people the itching can be severe.

In this example, questions that may be asked of a patient are illustrated in the "Pityriasis Rosea Telephone Script" seen in following Exhibit D.

Exhibit D
Telephone Script for Pityriasis Rosea

"Welcome to the Enigami symptom rating system!"
(English and Spanish) "If this is an emergency, please hang up and dial 911."
"If you prefer English, press 1. If you prefer Spanish, press 2."
"Please enter your Colorado Medicaid or Password."
"While answering, remember, 1 is very poor and 9 is very good unless explained differently during the question."
"If you wish to have a questions repeated, press the pound sign."
"Has your 'herald' or 'mother patch' begun to fade or disappear? Press 1 for yes and 2 for no."
"On a scale of 1 to 9 - how was your appetite yesterday?"
"On a scale of 1 to 9 - if you have had a fever, how was your fever? Report this by 1 on your phone signifying a single degree above your normal temperature, 2 signifying 2 degrees above your normal temperature, and so on. If you noticed no difference in temperature, please press zero."
"On a scale of 1 to 9 - please relate the degree of joint pain you had yesterday. If you had no joint pain, please press zero."
"On a scale of 1 to 9 - how much would you estimate the smaller patches, or rashes, have diminished?"
"On a scale of 1 to 9 - how was any itching yesterday?"
"On a scale of 1 to 9 - how many hours of artificial or natural sunlight do you think you were exposed to yesterday?"
"On a scale of 1 to 9 - if you were prescribed oral corticosteroids, did you take them as prescribed?"
"Finally, did you have an office visit this week? Press 1 for yes, and 2 for no."
"Thank you! Your responses have been recorded and indicate you are 'on the mend'. Congratulations! and goodbye."

Figure 7:
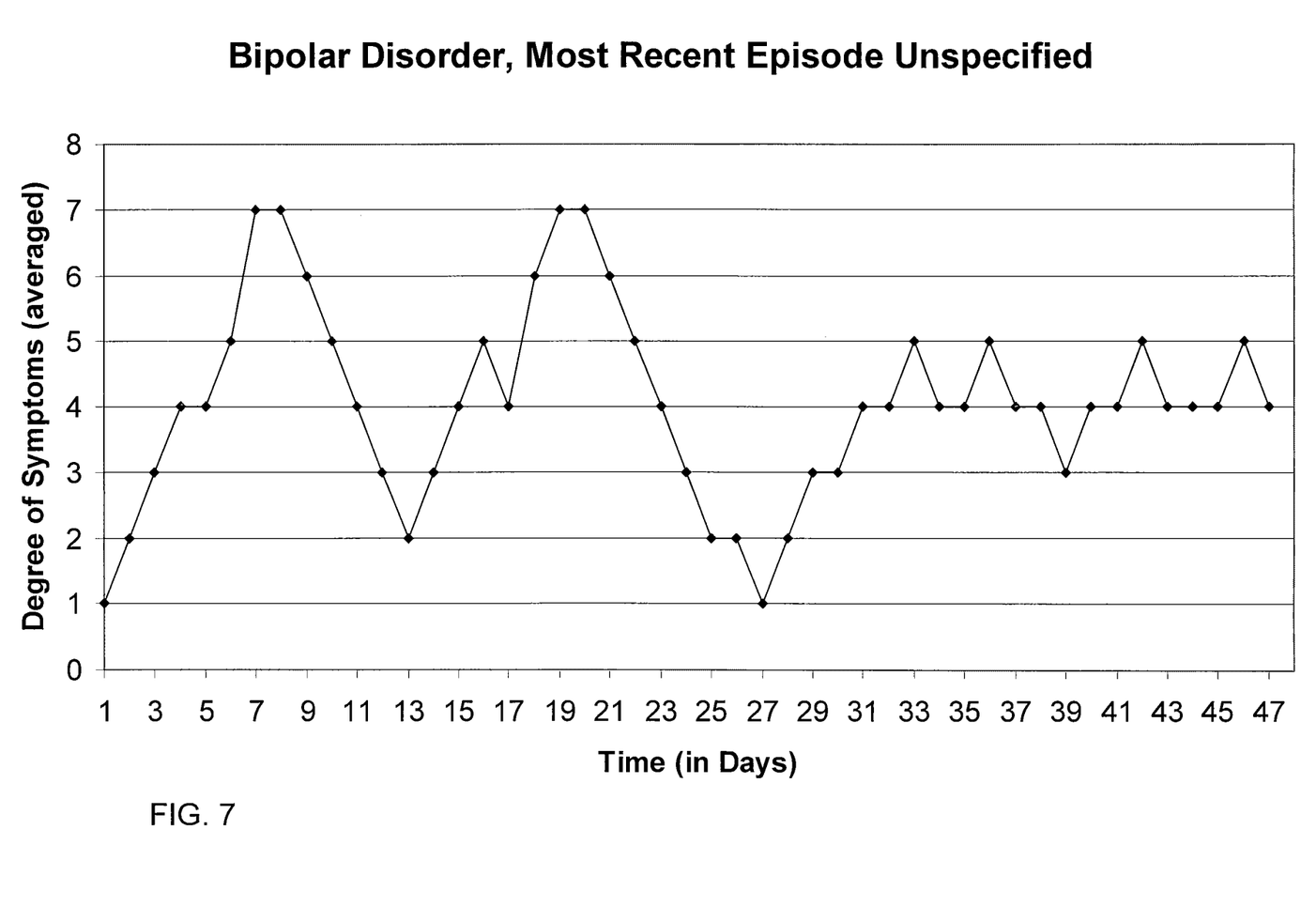
FIG. 7 is a report illustrating improving results in the treatment of a patient diagnosed with Bipolar Disorder.

Various other features and embodiments of the invention are illustrated in FIGS. 7 through 10 where, among other things, various reports that could be sent to the patient (consumer), to the provider (caregiver), to the provider organization (facility), and to the payer (insurer), are seen. In particular, FIG. 7 illustrates improving results in the treatment of Bipolar Disorder (symptoms stabilize and fluctuate less), and in particular, illustrates such results in a report that could be sent to a patient (as well as a provider). While not shown, a second report, similar to that in FIG. 7, could also be sent to a patient showing his/her progress relative to the average or typical progress for all patients treated in the past for the same disorder or condition. Such average information could be collected and stored by the system or be made available to the system via access to a central healthcare database.

Figure 8:
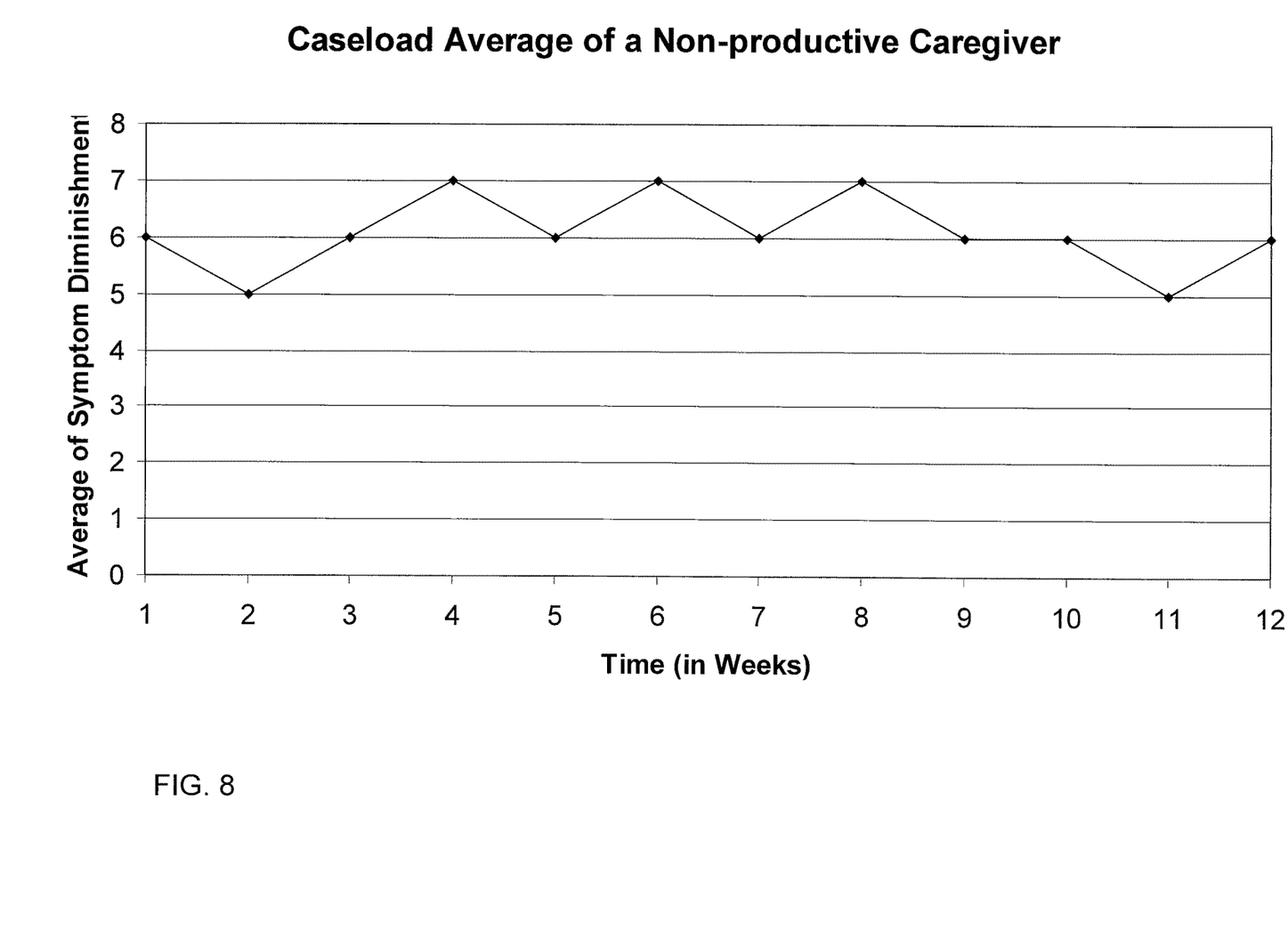
FIG. 8 is a report illustrating non-improving results across multiple patients for a single provider.

FIG. 8 illustrates non-improving results across multiple patients for a single provider (and hence non-productive results). A group mean value for all providers in this example would be a "4". This report could be sent to a provider (as well as a provider organization).

Figure 9:
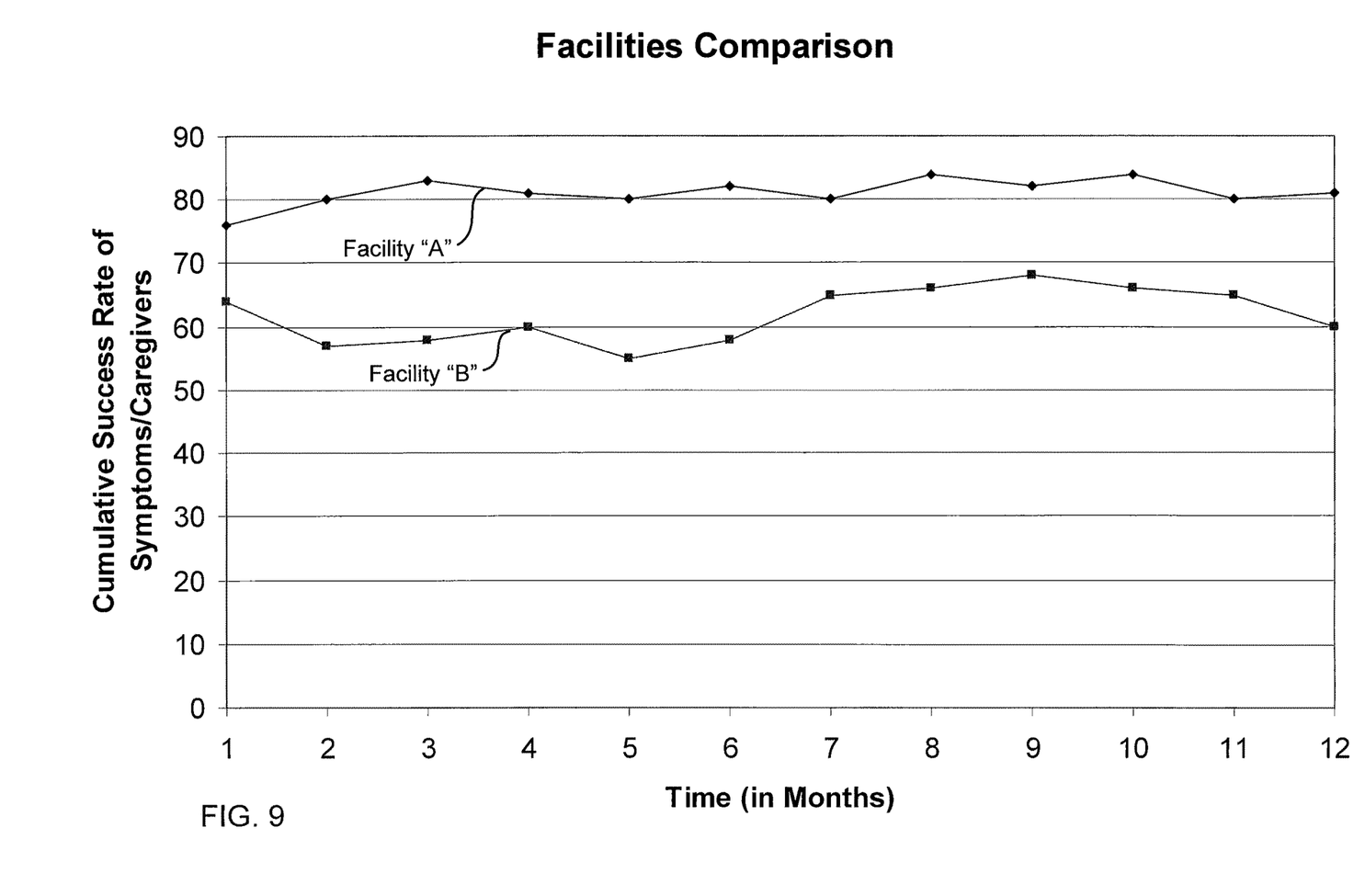
FIG. 9 is a report illustrating facility or organization comparisons for two different provider organizations.

FIG. 9 illustrates facility or organization comparisons for two different provider organizations. This report could be sent to a provider organization (facility) or to an insurer (payer). Among other things, the payer could make payments or provide incentives/bonsuses based on the reported results.

Other reports are possible. For example, reports could show not only the overall or averaged severity of symptoms (over time), but the severity of each symptom experienced by patients. This might permit the provider to modify treatment to address individual symptoms. Reports could also show the reported severity (over time) for a single provider for all of his/her patients having different diagnoses (illustrated separately for each diagnosis). This might reveal some providers as being better at treating some conditions than others. As a result, providers could be assigned to patients based on those providers having the best results for the anticipated diagnosis.

The network 100 and the reports generated by the network offer other features. For example, frequent monitoring of patient symptoms may more accurately and immediately indicate how patients are responding to medication. In the case of mental conditions or disorders, some patients may respond better without medication, and the reports may indicate progress based on therapy only. In other cases, more noticeable progress may be reported after a patient starts medication, and thus frequent and unnecessary (and expensive) one-on-one therapy sessions could be reduced. The network 100 also may improve treatment for patients that are located in rural areas, where trips to a provider may be time consuming and expensive for the patient. Such a patient may be able to receive initial treatment in person, and thereafter the provider may rely on periodic (e.g., daily) feedback from the patient via telephone 120 to monitor progress (perhaps in conjunction with periodic and direct calls from the provider), eliminating the need for frequent sessions in person (which might be resisted by the patient and result in prematurely ended treatment).

Also, for the weighting of symptoms discussed above (Example 1, and step 206, FIG. 2), the provider may establish both a first set of symptom weights based on the perceived importance to the patient and a second set of symptom weights based on importance to the provider, and then review separate reports based on each. This might permit the provider to measure progress in clinical terms (based on established symptoms and their clinically established importance to treatment) and also permit both the provider and the patient to measure progress based on the perceived importance or significance of symptoms to the patient (both the clinically established importance and the patient perceived importance may be relevant to treatment).

In addition, the feedback data for an individual patient may be collected and stored over time in database 112, and compared to large collections of general population data (e.g., data established using existing cohort or longitudinal studies, where the studies have been undertaken over many years and involve large numbers of people). The comparisons may assist in the diagnosis and treatment of the patient, using evidenced-based guidelines and treatment. Such comparisons may also be presented in reports to the patient (or provider) to illustrate treatment progress relative to general population or to the progress of other patients having similar symptoms and diagnoses. The general population data could be resident in database 112 or in other databases (not shown) accessible via network 128.

As should be appreciated, the system 110 permits reports to be created, modified, or customized based on the needs of patients, providers, provider organizations, and payers.

Figure 10:
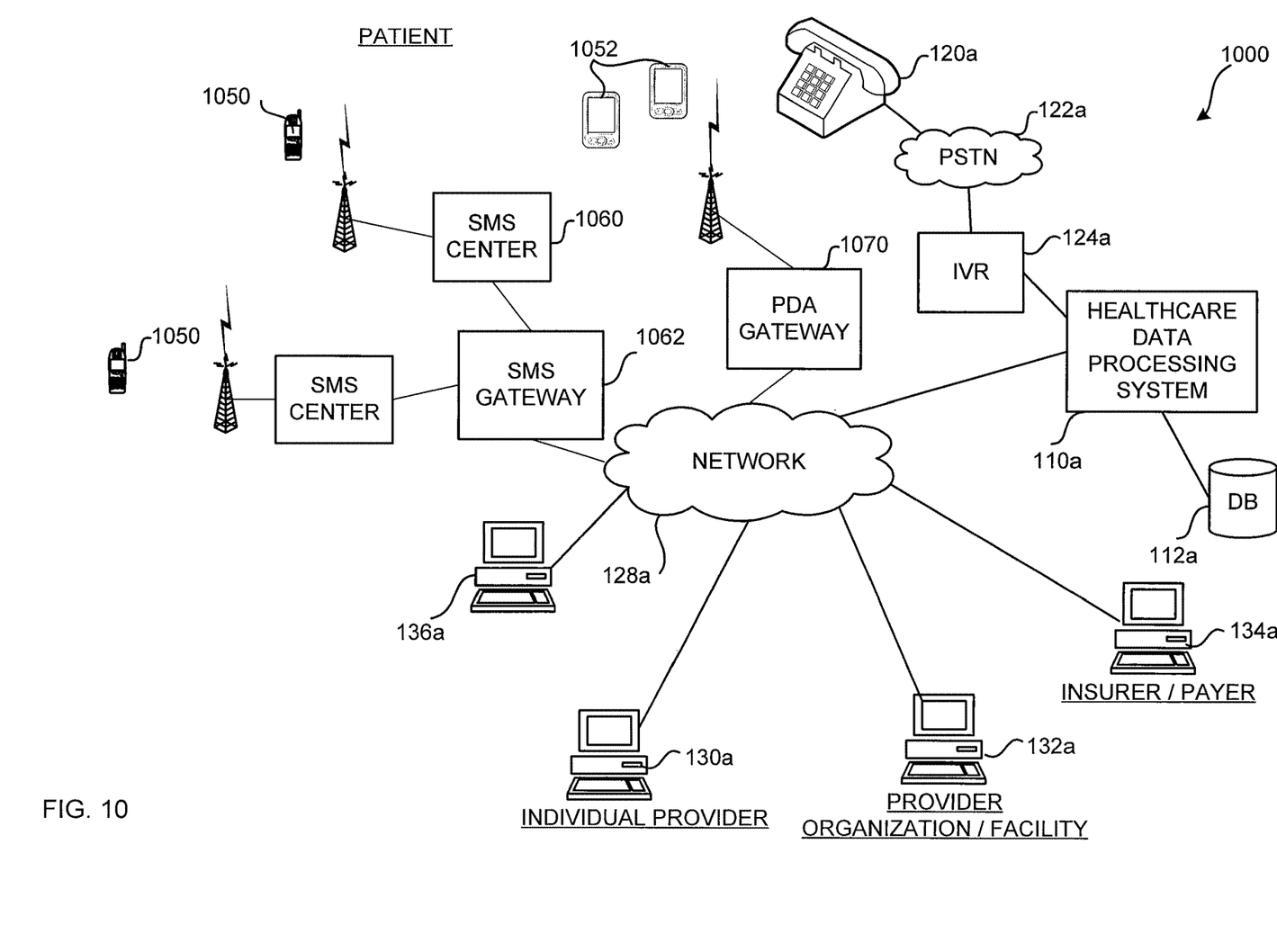
FIG. 10 is a block diagram of a healthcare data network in accordance with an alternative embodiment of the invention.

FIG. 10 illustrates another embodiment, namely a heath data network 1000 in which symptom data is collected, processed, measured and reported, using mobile device text messaging or emails in lieu of or in addition to responses or entries at a traditional telephone.

As seen in FIG. 10, the network 1000 includes a healthcare data processing system 110a (and associated database 112a), telephones 120a, a telephone network (PSTN) 122a, an IVR system 124a, a network (the Internet) 128a, and computer systems 130a, 132a, 134a and 136a, all of which operate in a manner similar to the like-referenced devices described in conjunction with FIG. 1. In addition, there are seen mobile phones 1050 and personal digital assistants (PDAs) 1052. The mobile phones 1050 are connected via SMS (Short Message Service) centers 1060 and an SMS gateway 1062 to the Internet (network 128) and the PDAs 1052 are connected via a PDA gateway 1070 to the Internet.

The SMS gateway 1062 converts emails (sent via the Internet) into SMS text messages, which are in turn routed to a destination mobile phone (enabled to receive text messages) via the SMS centers 1060. The SMS centers are maintained by a mobile or text messaging service to which mobile phone users subscribe. The PDA gateway 1070 is maintained by a PDA service (such a Blackberry®, Palm®, etc.) and converts email (sent via the internet) into messages adapted to be displayed at one of the PDAs 1052. Networks for handling emails and transmitting them to end users as text messages or PDA messages are well know. Reference can be had, as examples only, to U.S. Pat. No. 7,209,950, issued to Bennet et al., U.S. Pat. No. 7,079,524, issued to Bantukul et al., U.S. Pat. No. 7,092,370, issued to Jiang et al., and U.S. Pat. No. 7,103,372, issued to Kupsh, each of which is hereby incorporated by reference.

In the network 1000, after a patient has visited a healthcare provider and a diagnosis has been made, and the symptoms and weights for those symptoms have been established, the patient (and/or provider) may elect the most convenient or effective way to obtain feedback from the patient. The patient may elect to receive calls at a telephone 120a (as described earlier in connection with FIGS. 1 and 2). Alternatively, the patient may elect to receive emails or text messages (at the patient computer 136a, phone 1050 or a PDA 1052). One advantage to messages at the computer 136a, phone 1050 or PDA 1052 is that, after entry of feedback, the system 110a may respond with additional information or links based on the feedback. For example, if a patient diagnosed with dysthymia (Exhibit A above) provides feedback indicating improvement in all symptoms other than sleeping problems, the system 110a may be programmed to provide a subsequent email message with helpful information on improving sleep, or provide a link to a website with such information that can be displayed at the computer 136a, cell phone 1050 or PDA 1052.

Other features are also possible, such as the system 110a determining the need for a follow-up appointment with the provider (based on symptom severity or the length of the time since the last appointment), and using a calendaring program or similar feature at the system 110a to automatically suggest appointment times (in messages to the patient at the computer 136a, phone 1050 or PDA 1052), and then to confirm an appointment after an appointment time has been selected by the patient.

The network 1000 permits the method for collecting feedback to be varied from time-to-time according to the desires of the patient or the need for more effective collection. For example, if a patient has initially selected data messages (text or email messages) for collection of feedback, and if the patient does not respond to such messages (or if the data appears to be ambiguous or unusable), then the system 110a may automatically change the communications to an automated phone call. The patient may also select a back-up method for feedback, e.g., change from email at the PC 136a to a phone call or text message at phone 1050 when the patient is traveling away from his/her home.

Other options may be easily implemented in network 1000, such as the system 110a sending messages requesting feedback at times based on when symptoms may be at their worst or best, or when most indicative of the patients' progress. Messages may also be sent at random or rotating times to improve the quality of the feedback.

In some embodiments, other data may be collected in addition to or in lieu of the symptom data entered by the patient at one of the user devices (120a, 136a, 1050 and 1052). For example, wireless devices that are "worn" by the patient and that periodically monitor patient physical conditions (e.g., cardiovascular data) may be transmitted to the system 110, weighted (if appropriate), and combined with other patient entered data to generate reports.

Also, while disorders and conditions and their associated symptoms illustrated by way of example herein are taken from currently used medical/psychiatric references (e.g., Diagnostic and Statistical Manual of Mental Disorders [DSM-IV-TR®] and Merck Manual of Medical Information and the International Classification of Diseases [ICD-9-CM]), it should be appreciated such information may change to reflect current professional standards (e.g., as may appear in subsequent revisions to such references), or can be taken from other reliable or professionally accepted sources currently in use or that may be used in the future.

While a detailed description of presently preferred embodiments of the invention has been given above, various alternatives, modifications, and equivalents will be apparent to those skilled in the art without varying from the spirit of the invention.

What is claimed is:

1. A method comprising:
   retrieving one or more symptoms corresponding to a diagnosis for a first patient;
   periodically collecting patient-self-assessment data from the first patient relating to patient-self-assessment of the one or more symptoms by:
      establishing data messaging as a first method of collecting the patient-self-assessment data from the first patient via a data messaging device;
      determining that the data messaging method of collecting the patient-self-assessment data does not meet a predetermined standard; and
      changing from the data messaging method of collecting the patient-self-assessment data to an interactive voice response system method of making telephone calls to the first patient to collect the patient-self-assessment data because the data messaging method of collecting the patient-self-assessment data does not meet the predetermined standard;
   utilizing the interactive voice response system to periodically check that the telephone calls are being accepted by the first patient and that responses are being submitted by a telephone of the first patient;
   storing the collected patient self-assessment data on a first computer database;
   wherein when the patient-self-assessment data is collected from the first patient via self-reporting by the first patient the first patient is located remotely from the caregiver and located remotely from the facility of the caregiver;
   processing with a computer the collected patient-self-assessment of the one or more symptoms data to measure progress of treatment;
   reporting with the computer the identity of the caregiver that provided treatment for the first patient and the measured progress of treatment of the first patient, based on the collected patient-self-assessment of the one or more symptoms data, to a healthcare organization that determines a relative position of the caregiver in relation to a peer group of the caregiver in treating the diagnosis;
   assigning the caregiver to treat a second patient with the diagnosis when the measured progress of treatment shows that the caregiver is better in treating the diagnosis relative to the peer group of the caregiver in treating the diagnosis.

2. The method of claim 1, wherein the step of periodically collecting data from the first patient comprises an automated call to the first patient to collect symptom data.

3. The method of claim 2 and further comprising:
   periodically checking to make sure that the automated call is being accepted and that data is being entered by the first patient.

4. The method of claim 1 and further comprising:
   reporting the identity of a caregiver that provided treatment for the first patient and the measured progress of treatment of the first patient, based on the collected patient-self-assessment of the one or more symptoms data, to a utilization review entity that performs database based utilization review of the caregiver that provided treatment to the first patient, wherein the utilization review is based at least in part upon the collected data from the first patient relating to patient-self-assessment of the one or more symptoms.

5. The method of claim 1 wherein the healthcare organization determines a caregiver performance rating for the caregiver.

* * * * *